United States Patent [19]

Winkley et al.

[11] 4,001,216

[45] Jan. 4, 1977

[54] AMINOALKYL ETHERS OF 2,2'- AND 3,3'-DIHYDROXYDESOXYBENZOIN

[75] Inventors: Michael W. Winkley, Malvern; Gerhard R. Wendt, Havertown, both of Pa.

[73] Assignee: American Home Products Corporation, New York, N.Y.

[22] Filed: Oct. 30, 1975

[21] Appl. No.: 627,487

[52] U.S. Cl. ............... 260/239 B; 260/293.64; 260/239 BF; 260/326.5 G; 260/570.7; 260/326.5 A; 260/592; 260/326.5 S; 424/244; 424/267; 424/274; 424/330; 424/199
[51] Int. Cl.² ........................................ C07D 295/08
[58] Field of Search ... 260/239 B, 239 BF, 326.5 G, 260/293.64, 326.5 G, 326.5 A, 326.5 S

[56] References Cited

UNITED STATES PATENTS

| 3,207,788 | 9/1965 | Schumann | 260/239 B |
| 3,449,418 | 6/1969 | Werner | 260/239 B |

FOREIGN PATENTS OR APPLICATIONS

| 164,700 | 8/1955 | Australia | 260/293.8 |
| 40-27177 | 11/1965 | Japan | 260/293.8 |

*Primary Examiner*—Alton D. Rollins
*Assistant Examiner*—Mark L. Berch
*Attorney, Agent, or Firm*—David E. Frankhouser

[57] ABSTRACT

Dialkylaminoalkyl ethers of 2,2'- and 3,3'-dihydroxydesoxybenzoin are prepared by reacting the dithallium salt of 2,2'- or 3,3'-dihydroxydesoxybenzoin with a dialkylaminoalkyl chloride. The products have antiarrhythmic activity.

2 Claims, No Drawings

AMINOALKYL ETHERS OF 2,2'- AND 3,3'-DIHYDROXYDESOXYBENZOIN

This invention relates to chemical compounds classified in the art of organic chemistry as aminoalkylethers of 2,2'- and 3,3'-dihydroxydesoxybenzoin having useful pharmacological activity. The compound 5,5'-dichloro-2,2'-bis(2-diethylaminoethoxy)benzil is described by J. Finkelstein and S. M. Linder, *J. Amer. Chem. Soc.*, 71, 1010 (1949).

The invention sought to he patented comprises compounds having the molecular formula:

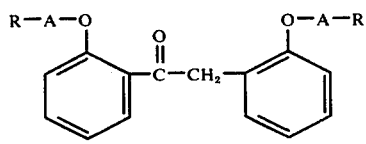 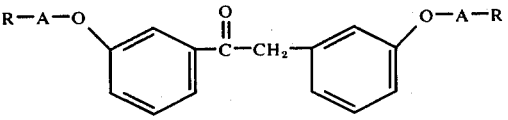

wherein A is a divalent aliphatic hydrocarbon radical of the formula

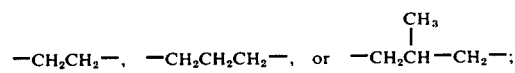

and R is a substituted amino group of the formula

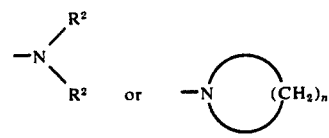

wherein $R^2$ is methyl, ethyl, propyl, or isopropyl, and $n$ is the number 4, 5, 6, 7, or 8; and the non-toxic, pharmaceutically acceptable acid addition salts thereof.

The compounds of Formula I and II in standard pharmacological test procedures elevate the electrical fibrillatory threshold of anesthetized dogs evidencing usefulness as antiarrhythmic agents. In addition, the compounds inhibit ADP-induced blood platelet aggregation indicating usefulness as antithrombitic agents.

The compounds of Formula II can be prepared by condensing a dithallium salt of 3,3'-dihydroxydesoxybenzoin with an appropriate di(substituted) aminoalkyl chloride in refluxing toluene or toluene-N,N-dimethylformamide (DMF). 3,3'-Dihydroxydesoxybenzoin can be prepared in two steps from 3,3'-dihydroxybenzil by: (a) reducing 3,3'-dihydroxybenzil with tin-hydrochloric acid at steam-bath temperature to give 1,2-bis(-hydroxyphenyl)-2-hydroxy-ethanone, and (b) reducing the ethanone intermediate with chromic sulfate and zinc dust in water-ethanol. 3,3'-Dihydroxydesoxybenzoin can also be prepared by the direct reduction of 3,3'-dihydroxybenzil with zinc in aqueous DMF at reflux temperature.

Alternatively, the compounds of Formula II as well as the compounds of Formula I can be prepared by reducing a 2,2'- or 3,3'-dihydroxybenzil derivative containing an appropriate di(substituted)aminoalkyl substituent (R — A). The reduction is carried out by heating the substituted benzil starting material with zinc at reflux temperature in aqueous DMF for at least 4 days. The starting substituted benzils are described in the copending application of Gerhard R. Wendt and Michael W. Winkley, Ser. No. 513,354, now U.S. Pat. No. 3,935,191 filed Oct. 9, 1974. In general, the benzils can be prepared by condensing a dithallium salt of 2,2'- or 3,3'-dihydroxy-benzil with an appropriate di(substituted)aminoalkyl chloride in refluxing toluene or toluene-DMF.

The compounds obtained in the free base form can be conveniently isolated and purified in the form of an acid addition salt. Such salts are made by conventional methods such as by combining the base and a suitable acid in a reaction-inert organic solvent.

Dithallium salts are prepared by reaction of 3,3'-dihydroxydesoxybenzoin or of 2,2'- or 3,3'-dihydroxybenzil with thallium (I) ethoxide in an organic solvent, for example benzene, toluene, or ethanol-benzene. The salt precipitates from the reaction medium and can be isolated by filtration. [See Taylor et al., *J. Am. Chem. Soc.*, 90, 245 (1968) and Paquet et al., *Can. J. Chem.*, 51, 3855 (1973)].

It is apparent that the compounds of Formula I or II are symmetrically substituted, i.e., the same A or R group is substituted at each oxygen attached to the benzil nucleus.

For pharmacological purposes the compounds can be employed in the form of acid addition salts with non-toxic and pharmaceutically acceptable acids. Such acids will be apparent to one skilled in the art. Appropriate salts are those formed from either inorganic or organic acids, for example hydrochloric, hydrobromic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, benzenesulfonic, p-toluenesulfonic, and 2-naphthalene-sulfonic.

The methods of making and using the compounds of the invention are illustrated in the following examples:

EXAMPLE I

2-Hydroxy-1,2-bis(3-hydroxyphenyl)ethanone

To a hot stirred solution of 3,3'-dihydroxybenzil (5 g.) in water (200 ml) and tin (30 mesh) was slowly added concentrated hydrochloric acid (10 ml.). Heating on a steam bath with efficient mechanical stirring was continued for 1 hour. Thin layer chromatography on Silica AR 7GF plates (Mallinckrodt) with chloroform-methanol (9:1) showed the reaction was largely complete after 15 minutes. The mixture was filtered, while hot, through Celite and the filtrate was evaporated to smaller volume. The resulting crystals (4.60 g.), m.p. 159°–162° were recrystallized from hot water with decolorization to give white crystals, m.p. 173°–175°, M⁺ 244 (E. I. mode), pmr (DMSO-$d_6$) δ 5.97 [s, —C$\underline{H}$(OH)].

Analysis for: $C_{14}H_{12}O_4$. Calculated: C, 68.84; H, 4.95. Found: C, 68.44; H, 5.34.

EXAMPLE II 1,2,Bis(3-hydroxyphenyl)ethanone

2-Hydroxy-1,2-bis(3-hydroxyphenyl)ethanone was reduced by the procedure of M. Pisova and M. Soncek

[Coll. Czech, *Chem. Comm.*, 38, 3876 (1973)]. A mixture of 2-hydroxy-1,2-bis(3-hydroxyphenylethanone (18 g.) chromic sulfate hydrate (20.9% Cr; 60 g.), zinc dust (49 g.) and water-ethanol (1:1, 1 liter) was stirred under an atmosphere of nitrogen for 11 hours. The mixture was diluted with water and extracted with three portions of ethyl acetate. The organic solution was washed with saturated brine solution and dried over magnesium sulfate. The solution was concentrated and the product crystallized from ethyl acetate-benzene (seeding); yield: 8.51 g., m.p. 155°–156°.

The mother liquor was purified by chromatography on a "dry" column of silica gel. The faster moving impurities were removed by elution with chloroform and the product was eluted with chloroform-ethyl acetate (9:1). The appropriate fractions were evaporated and the residual syrup crystallized as above to give an additional 2.81 g. (m.p. 153°–156°) of crude product. Recrystallization of the two crops gave 9.5 g. of pure product; m.p. 157°–158°; pmr (DMSO-$d_6$) δ 4.15 (—CO$\underline{C}H_2$—).

Analysis for: $C_{14}H_{12}O_3$. Calculated: C, 73.67; H, 5.30. Found: C, 73.90; H, 5.35.

EXAMPLE III 1,2-Bis[3(2-diethylaminoethoxy)phenyl]ethanone

To a stirred solution of 1,2-bis(3-hydroxyphenyl)ethanone (2.28 g.) in absolute ethanol (50 ml.) was added thallous ethoxide (5.0 g.) in benzene (50 ml.). The mixture was stirred for 15 minutes and the precipitate was collected on a filter. The filter cake was washed consecutively with ethanol, benzene and ether. The yield of dithallium salt was 6.33 g.

To an azeotropically dried suspension of the dithallium salt (6.0 g.) of 1,2-bis(3-hydroxyphenyl)ethanone in toluene (200 ml.) was added dropwise 18 ml. of a solution of diethylaminoethyl chloride (160 g. per liter) in toluene. After the mixture had been stirred and heated under reflux for 2 ½ hours a further 8 ml. of reagent solution was added and stirring and heating under reflux were then continued for a further 1 ½ hours. After cooling the precipitate was collected by filtration and washed with toluene. The filtrate and washings were evaporated to a syrup which was evaporated further under oil pump vacuum. The syrup was dissolved in chloroform and the solution was applied to a column (33 × 3.7 cm.) of alumina (Woelm, drycolumn grade) prepacked in chloroform. The column was eluted with chloroform and the appropriate fractions were collected. The frantionation was monitored visually and by tlc on "ALOX-25 UV 254" plates with ethyl acetate as developer. Care was taken to avoid collecting an additional colored component which issued from the column in later fractions. The homogeneous fractions were pooled and evaporated to give 1.77 g. of syrup.

To the above material (1.77 g.) in methanol (50 ml.) was added anhydrous citric acid (1.6 g.) and further citric acid until a definitely acidic pH value was obtained. The solution was evaporated and crystallized from methanol-ether to give 2.98 g., m.p. >90° dec. Two crystallizations from methanol-ether gave the title product as the dicitrate (1.33 g.), m.p. 102°–104°; MH$^+$ 427 (C.I. mode).

Analysis for: $C_{38}H_{54}N_1O_{17}$. Calculated: C, 56.29; H, 6.71; N, 3.45. Found: C, 56.56; H, 6.83; N, 3.63.

EXAMPLE IV 1,2-Bis[3-(3-dimethylaminopropoxy)phenyl]ethanone

To an azeotropically dried suspension of the dithallium salt (18 g.) of 1,2-bis(3-hydroxyphenyl)ethanone in toluene (500 ml.) was added dropwise 63 ml. of a solution (65.5 g. per liter) of dimethylaminopropyl chloride in toluene followed by 100 ml. of N,N-dimethylformamide. After the mixture had been stirred and heated under reflux for 1 hour a further 30 ml. of reagent was added. After a further 6 hours, 30 ml. more of reagent was added. The mixture was stirred and heated for a further 3 hours. After cooling, the precipitate was collected on a filter and washed with toluene. The filtrate and washings were evaporated to a syrup which was evaporated further under oil pump vacuum. The syrup was dissolved in chloroform and applied to a column (5.5 × 44 cm.) of alumina (Woelm, dry column grade) prepacked in chloroform. The column was eluted with chloroform and the fractionation was monitored visually and by tlc on "ALOX-25 UV 254" plates with ethyl acetate as developer. One hundred milliter fractions were collected and fractions 17–21 were pooled and evaporated to give 4.1 g. of a homogeneous syrup free of a slower moving colored contaminant.

To the above material (4.1 g.) in warm ethanol (50 ml.) was added 2-naphthalenesulfonic acid monohydrate (2.5 g.) and further 2-naphthalenesulfonic acid until pH 4–5 was reached. Addition of ether, followed by scratching and cooling produced 5.99 g. of crystals, m.p. 102°–105°. The product was dissolved in methanol and the solution was decolorized. The solution was evaporated to a syrup and the syrup was coevaporated with absolute ethanol. Water was added to the syrup to cause spontaneous crystallization. Ethanol and ether were then added. This crystalline material was collected and recrystallized in the same manner to give 5.3 g. of the title product as the bis(2-napthalenesulfonate), sesquihydrate, m.p. 102°–105°; MH$^+$ 399 (C.I. mode on regenerated free base).

Analysis for; $C_{44}H_{50}N_2O_9S_2$. 1.5 $H_2O$. Calculated: C, 62.76; H, 6.34; N, 3.33; S, 7.62; $H_2O$, 3.21. Found: C, 63.09; H, 6.18; N, 3.32; S, 7.88; $H_2O$, 3.21.

EXAMPLE V 1,2-Bis(3-hydroxyphenyl)ethanone

A mixture of 3,3'-dihydroxybenzil (3.0 g.) and powdered zinc (5.0 g.) in N,N-dimethylformamide (25 ml.) and water (10 ml.) was stirred and heated under reflux for 6 hours. The cooled mixture was filtered through Celite and the filtrate was evaporated under oil pump vacuum to give a syrup. The syrup was dissolved in ethyl acetate and the solution was washed consecutively with dilute hydrochloric acid and saturated brine (thrice). The dried ($MgSO_4$) solution was evaporated to smaller volume and benzene was added. A by-product (0.45 g., m.p. 225°–228°) crystallized on standing. The mother liquor was evaporated to a syrup which was crystallized by seeding from ethyl acetate benzene to give the title product (0.88 g., m.p. 151°–154°) which was shown to be identical with material produced from the two stage reduction (1, Sn/HCl; 2, Zn/chromic sulfate).

The by-product [1,2-bis(3-hydroxyphenyl)-1,2-ethanediol] was recrystallized from ethyl acetate-benzene to give pure material, m.p. 229°–231°, pmr (DMSO-$d_6$) 4.50 (s, —H$\underline{C}$OH$\underline{C}$HOH—).

Analysis for: $C_{14}H_{14}O_4$. Calculated: C, 68.28; H, 5.73. Found: C, 67.97; H, 5.85.

EXAMPLE VI 1,2-Bis[o-(2-(1H-hexahydroazepin-1-yl)ethoxy)-phenyl]ethanone

A mixture of 2,2'-bis(2-hexamethyleneiminoethoxy)benzil (free base 12.0 g.) and powdered zinc (24 g.) in N,N-dimethylformamide (120 ml.) and water (40 ml.) was stirred and heated under reflux in a nitrogen atmosphere for 4 days. The cooled mixture was filtered through Celite and the filter pad was washed with N,N-dimethylformamide. The filtrate and washings were evaporated under oil pump vacuum to a syrup. The syrup was dissolved in benzene containing a small volume of chloroform. The solution was applied to a column (57 × 5.6 cm.) of alumina (Woelm, dry column grade) prepacked in benzene. The column was eluted consecutively with benzene and benzene-chloroform (4:1). The fractionation was monitored by tlc on ALOX UV 254 plates (Brinkmann) with chloroform-ethyl acetate (7:3) as developer. Fractions containing the faster moving colorless component were evaporated to a syrup. The syrup was extracted with heptane and the solution decolorized. Evaporation produced 3.7 g. of a homogeneous syrup. The mass spectrum (C.I. mode) showed a parent peak at 479 and no peaks at 493 and 495 (benzil and benzoin).

Analysis for: $C_{20}H_{42}N_2O_3$. Calculated: C, 75.27; H, 8.84; N, 5.85. Found: C, 74.61; H, 9.17; N, 5.91.

EXAMPLE VII

The antiarrhythmic activity of the compounds of the invention is demonstrated and ellicited by the following test method:

The heart of an anesthetized dog is exposed by a left thoracotomy. Bipolar electrodes are sutured to the epicardial surface of the left ventricle. The heart is stimulated with square wave pulses of 3 msec. duration and frequency of 60 Hz. for periods of 5 sec. Voltage is increased until fibrillation ensues. The heart is then defibrillated by DC countershock and the procedure repeated at 10 min. intervals. Drugs are administered i.v. over periods of 3 min. and fibrillatory threshold examined 10 min. after start of injection of each dose. Effective antiarrhythmic agents elevate the fibrillatory threshold.

When tested as set forth above the compounds described in Examples III and IV elevate the electrical fibrillatory threshold at a dose of 20 mg/kg. body weight.

EXAMPLE VIII

Platelet aggregation is an initial step in thrombus formation, and it is considered that compounds which prevent aggregation or reduce platelet adhesiveness inhibit one of the initiation steps of the arteriosclerotic process. The effect of drugs on aggregation is measured in platelet rich plasma (PRP) to which adenosine diphosphate (ADP), which markedly increases aggregation in vitro, is added. Human blood is collected from fasted normal blood donors in siliconized 50 ml. Vacutainers that contain 3.8% sodium citrate. Centrifugation of 500 g. for 3 minutes at 5° C. separates the red blood cells from the PRP. The supernatant PRP is pipetted off and the remainder is centrifuged at 1000 g. for 10 minutes at 25° C. to obtain platelet poor plasma for standardization of the automated Payton aggregometer. In the running of the platelet aggregation test a cell containing 1.0 ml. of PRP is stirred at 1,100 rpm. and the test compound is added in 0.2 ml. of buffered saline to give an initial concentration of $5 \times 10^{-4}$M. After 3 minutes, a concentration of ADP predetermined to yield marked platelet aggregation (2 to 4 $\mu$M) is added in 0.1 ml. of buffered saline. The curve of light transmission at 610 m$\mu$ is followed for 6 minutes. Compounds found to be active at the initial concentration are run at lower concentrations.

When tested as set forth above the compound described in Example II gave 50% inhibition of platelet adhesiveness at a concentration of $6.9 \times 10^{-5}$M. while the compound described in Example IV gave 50% inhibition at a concentration of $3.6 \times 10^{-5}$M.

What is claimed is:
1. A compound of the formula

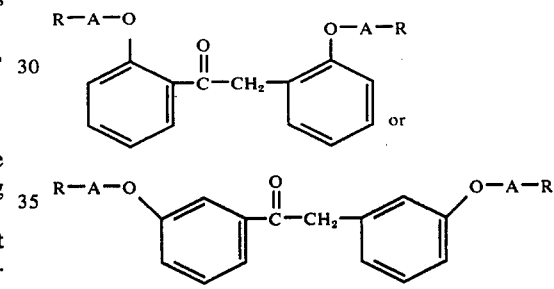

wherein A is a divalent aliphatic hydrocarbon radical of the formula $$-CH_2CH_2-, \quad -CH_2CH_2CH_2-, \quad or \quad -CH_2\overset{\overset{\displaystyle CH_3}{|}}{CH}-CH_2-;$$

and R is identically a substituted amino group of the formula

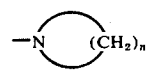

wherein n is the number 4, 5, 6, 7, or 8; and the nontoxic, pharmaceutically acceptable acid addition salts thereof.

2. A compound as defined in claim 1 which is 1,2,-bis[o-(2-(1H-hexahydroazepin-1-yl)ethoxyl)phenyl]ethanone.

* * * * *